United States Patent [19]

Magni et al.

[11] Patent Number: 5,859,360
[45] Date of Patent: Jan. 12, 1999

[54] METHOD AND DEVICE FOR CONTROLLING FLOW RATE OF CARRIER GAS IN CHROMATOGRAPHIC APPARATUS

[75] Inventors: Paolo Magni, Besana Brianza; Giacinto Zilioli, Cernusco; Fausto Munari, Milan; Sorin Trestianu, Rodano; Pieralbino Colombo, Treviglio, all of Italy

[73] Assignee: Fisons Instruments S.P.A., Italy

[21] Appl. No.: 646,308

[22] PCT Filed: Sep. 15, 1995

[86] PCT No.: PCT/EP95/03627

§ 371 Date: May 15, 1996

§ 102(e) Date: May 15, 1996

[87] PCT Pub. No.: WO96/08718

PCT Pub. Date: Mar. 21, 1996

[30] Foreign Application Priority Data

Sep. 16, 1994 [IT] Italy ................... MI94A1889

[51] Int. Cl.$^6$ ..................................... C07C 1/135
[52] U.S. Cl. ............. 73/19.05; 73/23.35; 73/23.42
[58] Field of Search ............... 73/19.05, 23.35, 73/23.36, 23.37, 23.38, 23.39, 23.4, 23.42

[56] References Cited

U.S. PATENT DOCUMENTS 5,339,673  8/1994  Nakagawa et al. .............. 73/23.36

FOREIGN PATENT DOCUMENTS 0 329 290  8/1989  European Pat. Off. .
0 396 884  11/1990  European Pat. Off. .
4184167  7/1992  Japan .

OTHER PUBLICATIONS

Patent Abstract of Japan, vol. 15, No. 460 (P–1278), 21 Nov. 1991.

*Primary Examiner*—Scott W. Houtteman
*Attorney, Agent, or Firm*—Millen, White, Zelano & Branigan, P.C.

[57] ABSTRACT

There is provided a method and apparatus for controlling the carrier gas flow through a gas chromatographic apparatus with capillary column subjected to variations in temperature, through control of feeding pressure achieved following computerized processing of the equation of the carrier flow rate as a function of inlet pressure, column temperature and system structural parameters, including preliminary determination of the system parameters through detection of pressure, temperature and flow rate values in stabilized conditions of carrier passage through apparatus and calculation of a constant representing said parameters on the basis of values detected and in application of the aforesaid equation; storage of aforesaid constant; utilization of constant in the mentioned equation for controlling carrier flow rate through calculation and control of its feeding pressure during utilization of the gas chromatographic apparatus.

7 Claims, 2 Drawing Sheets ns to which the
METHOD AND DEVICE FOR CONTROLLING FLOW RATE OF CARRIER GAS IN CHROMATOGRAPHIC APPARATUS This is the national filing of international application Ser. No. PCT/EP95/03627, filed Sep. 15, 1995.

1. Technical Field

The present invention relates to a method and a device for controlling pressure and flow rate of carrier gas in apparatus for gas chromatographic analysis with capillary column.

2. Background Art

As it is well known analysis time and separation efficiency and response of detecting system in an apparatus for gas chromatographic analysis are influenced not only by variations of temperature in the column, but also by variations of carrier gas flow rate passing through the column itself, variations that are in turn dependent on temperature. For this reason it has been endeavoured, both in past and in recent times, to control and program besides the temperature in column, the carrier gas flow rate as well.

Actually, one of the most usual problems arising in capillary gas chromatography is caused by the variation of carrier gas flow rate while programming temperature in the column, this programming being required to separate the samples containing components with a high range of volatility and largely utilized in practice. While programming temperature, the viscosity of the carrier gas increases and, if such gas is fed by constant pressure, its flow through the column decreases. This influences the response of gas chromatographic detectors sensitive to the flow rate, meaning that the response results variable as a function of the temperature program selected. Besides, a decrease in the flow rate of carrier gas increases analysis time and reduces the detectability of eluted components in the conclusive period of same analysis. Maintaining a constant flow rate of carrier gas at the column exit eliminates this inconvenience.

Feeding carrier gas with constant flow rate, instead of feeding at constant pressure, does not present a solution to the problem when the column operates in association with injectors of the split/splitless type, certainly well known, which present different exit lines open to the atmosphere. Maintaining a constant carrier flow at the entrance of the injector does not guarantee a constant flow through the column because the fluid resistance in the column increases along with oven temperature, whereas the other exits present unvaried fluid resistance.

For this and further reasons there is an ever increasing tendency to control carrier gas flow through the column not only and not always in order to keep it volumetrically constant, but also even to run a prefixed program of volumetric flow rate variation.

Harris & Habgood (Programmed Temperature Gas Chromatography, Wiley, N.Y.(1966) 23–31) recalled notably that the flow of a gas in a capillary column is ruled by Poiseuille's equation:

$$F_o^T = \frac{\pi d^4}{256 \eta L} \cdot \frac{p_i^2 - p_o^2}{p_o^2}, \quad (1)$$

in which the volumetric flow rate in $Fo^T$ outlet is correlated to inlet pressure $p_i$ and outlet pressure $p_o$, to inner diameter d and column length L, as well as to viscosity $\eta$ of the fluid, or rather of the carrier. As viscosity $\eta$ depends upon temperature, also flow rate $Fo^T$ varies according to temperature variation and the above mentioned publication presents semiempiric mathematic correlations to be applied so as to take into account the variations of viscosity with temperature, in order to achieve the desider control of flow rate, keeping in mind the temperature variations to which the column is subjected. In this way there is obtained the equation regulating the variations of inlet pressure as a function of the temperature to be applied to achieve determinate flow values at the exit of the column, equation that shall be called afterwards, in its various formulations "equation of carrier gas flow rate variation as a function of inlet pressure, of column temperature and system structural parameters". The volumetric flow rate at exit can be expressed as a function of the effective values of column temperature and of pressure outlet.

It is, however, more convenient to express it in pressure and temperature standard conditions (equations 2.07 and 2.08 in above mentioned document) as required for utilization of mass flow control devices present on the market. EP-A-396884 Hewlett Packard Company (corresponding to U.S. Pat. No. 4,994,096) relates to a method and apparatus for controlling carrier gas flow fate through control of inlet pressure taking temperature into account. This control is accomplished by applying the above mentioned equation, derived from Poiseulle's equation, and by computer processing the value of inlet pressure each time required in order to get the desired flowrate. Obviously, to apply such equation it is necessary to enter the so-called system data (column inner diameter and length) and gas data (viscosity at column temperature and density in standard conditions).

According to the aforesaid patent application, al least part of these data are entered, prior to analysis, into computer via keyboard.

This entering via keyboard, especially for what concerns system data, implies however that the column should have exactly the length stated and an inner diameter exactly identical to the one indicated and constant in all its length, with a regular inner surface.

In practice, however, this does not occur, as the column may be shortened when it is mounted and above all it can have a length and/or a diameter different from the ones stated and may present inner irregularities. These variations influence the carrier flow and introduce differences, even considerable, with respect to the result of calculation performed on hypothesis of ideal flow.

DISCLOSURE OF THE INVENTION

Purpose of the present invention is to provide a method and device for controlling the flow of carrier gas, by controlling the pressure feeding in apparatuses for gas chromatography analysis with capillary column, which allow eliminating or at least reducing substantially errors entered because of differences between real and ideal conditions in the chromatographic column, besides the ones that may have been entered by operator.

To achieve what afore said, the method and apparatus according to the present invention require no more entering system data via computer keyboard, but a previous calculation of the constant representing them in the above defined equation, performed detecting values of the variables present in that equation (flow, pressure and temperature) in a stabilized condition of flow through a column.

More precisely, the invention is related to a method for controlling the carrier gas flow through a gas chromatographic apparatus with capillary column subjected to variations in temperature, through control of feeding pressure achieved following computerized processing of the equation of the carrier flow rate as a function of inlet pressure, column temperature and system structural parameters, comprising: preliminary determination at least of the system parameters through detection of pressure, temperature and flow rate values in stabilized conditions of carrier passage through apparatus and calculation of a constant representing said parameters on the basis of values detected and in application of the aforesaid equation; storage of aforesaid constant; utilization of constant in the mentioned equation for controlling the carrier flow rate through calculation and control of its feeding pressure during utilization of the gas chromatographic apparatus.

In Poseuille's equation (I) formulated before, one notices that there is a so-called system term that depends upon the column physical characteristics: $K_1 = \pi d^4/256\ L$, moreover a so-called gas term that is constituted by viscosity $\eta$ and can also be expressed as a function of standard viscosity and of standard temperature: (Harris & Habgood, above mentioned publication, eq.2.05) $\eta = \eta st\ (T/T_{st})^{0,7}$ wherein $\eta st$ and $T_{st}$ are respectively viscosity and temperature of gas in standard conditions (25° C.=298K, 1 atm).

The equation then reads:

$$F_o^T = K_1 \frac{1}{\eta st} \left(\frac{T_{st}}{T}\right)^{0,7} \frac{p_i^2 - p_o^2}{p_o} = K_1 K_2 \frac{p_i^2 - p_o^2}{p_o} \frac{1}{T^{0,7}}$$

According to the invention, it is poss.r)le to determine by calculation the only $K_1$ value, or product $K_1 \cdot K_2$, detecting the volume flow rate at the column exit.

As, however, it is advisable that the flow detector (as well as the inlet pressure detector) should be positioned upstream of the column and therefore of the injector, and as the present flow dCtectors detect in reality a mass flow (expressed in terms of volumetric flow in preset (standard) conditions of pressure and temperature), calculation of constant, which generally comprises both system data and gas data, can be performed as follows. From the ideal gas law we have:

$$Fst = F_o^T \frac{T_{st}}{T} \frac{p_o}{p_{st}}$$

where $F_{st}$ is the flowv rate in standard conditions ($T_{st}$=298° K, $P_{st}$=1 atm).

Applying this relation to (I) we get:

$$F_{st} = \frac{\pi d^4}{256 L \eta} \frac{pi^2 - po^2}{p_{st}} \frac{T_{st}}{T} \quad \text{(II)}$$

The gas viscosity $\eta$ variation with temperature can be calculated according to the followving relation (see Harris & Harbgood, afore said publication):

$$\eta = \eta_{st} \left(\frac{T}{T_{st}}\right)^{0,7}$$

in which $\eta_{st}$ is viscosity at T=298° K and p=1 atm
Therefore $$F_{st} = \frac{\pi d^4}{256 L} \frac{1}{\eta_{st}} \left(\frac{T_{st}}{T}\right)^{0,7} \frac{pi^2 - po^2}{p_{st}} \frac{T_{st}}{T}$$

Or better, gathering all constant terms:

$$F_{st} = \frac{\pi d^4}{256 L} \frac{1}{\eta_{st}} \frac{T_{st}^{1,7}}{p_{st}} \frac{pi^2 - po^2}{T^{1,7}} \quad \text{(III)}$$

-continued $$\text{Having } K = \frac{\pi d^4}{256 L} \frac{1}{\eta st} \frac{T_{st}^{1,7}}{p_{st}} \quad \text{(IV)}$$

equation (III) becomes:

$$Fst = K \frac{pi^2 - po^2}{T^{1,7}} \quad \text{(V)}$$

Therefore, the value of K can be calculated measuring entrance mass flow rate expressed as volume flow rate in standard conditions, column temperature, inlet pressure and outlet pressure and applying the previous equation $$K = \frac{F_{st} T^{1,7}}{pi^2 - po^2}$$

BEST MODE FOR CARRYING OUT THE INVENTION

Such value is then utilized for calculating inlet pressure so as to obtain the flow rate desired, by entering it into Poiseuille's equation, as it shall be better shown hereinafter with reference to the enclosed drawings.

BRIEF DESCRIPTION OF THE DRAWINGS

With reference to FIG. 1, the device outlined comprises, on line 10 of carrier gas feeding, a valve 11 electronically controlled to control the feeding pressure, a pressure detector 12 and a mass flow rate detector 13, all operating under control of a local electronic circuit 14, specifically of analog type, that sees to reading pressure and flow signals from detectors 12 and 13 and to generating a command signal for the valve, on the basis of effective and set values.

Figure 1:
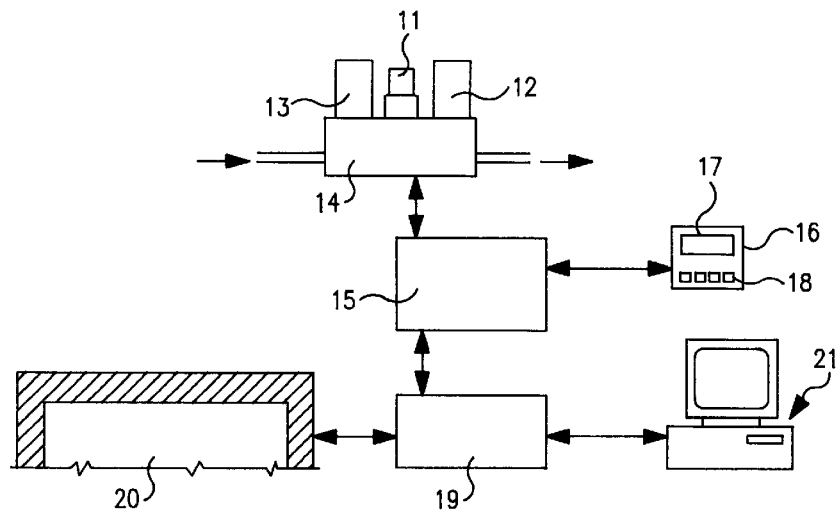
FIG. 1 shows in outline an example of gas cromatography analysis apparatus for the embodiment of the present invention.

Circuit 14 is on turn connected with control central circuit 15 that performs the analog/digital conversion of the pressure set and all other calculations required. Pressure and flow rate data, both effective and set, are shown in panel 16, bearing an indicator 17 to visualize pressure and flow values, as well as a keyboard 18 for setting desired data by operator. Circuit 15 is connected to CPU 19 to detect, from oven 20, the temperature signal necessary to perform calculations, as well as to allow in case a remote control, through personal computer 21:

The calculation of constant K, from equation (V) above quoted:

$$K = \frac{F_{st} \cdot T^{1,7}}{pi^2 - po^2} \quad \text{(VI)}$$

is performed detecting pressure and flow values 12 and 13 in stabilized conditions of carrier gas feeding and of thermic regulation of oven 20.

To be more precise, with reference to equation (VI), we have:

$F_{st}$=flow rate measured by detector 13 and brought back to standard conditions of temperature and pressure (25° C., 1 atm), taking into account the nature of carrier (hydrogen,nitrogen. helium etc.), information that is passed on to the system through a microswitch and is used to calibrate detector 13;

pi=absolute inlet pressure, measured by detector 12;

po=absolute outlet pressure, equal to 1 atm for gas chromatographic atmospheric detectors and equal to zero for detectors under vacuum (mass spectometer types);

T=absolute temperature of oven 20, as sent to CPU.

In practice, control circuit 15 commands a pressure value, receives pressure and flow rate signals from circuit 14, temperature signals from CPU 19 and performs calculation of constant K, which is then stored and utilized for calculating and controlling flow through pressure, in all subsequent analyses with same column and same carrier. For each analysis there is set a flow rate (or a variation of flow in time) through a command panel 16 (or through computer 21) and circuit 15 calculates each time, utilizing the effective value of the temperature and flow chosen, the pressure required to obtain such flow, by the same equation (V) transcribed as follows:

$$pi = \sqrt{po^2 + \frac{F_{sti}T^{1,7}}{K}}$$

wherein $F_{sti}$ is the flow rate set, expressed in standard conditions.

Remark that the determination of parameters to calculate constant K is to be performed with the system completely closed towards the exterior, meaning that the carrier gas flow rate fed in equilibrium conditions for determining aforesaid parameters is to be exactly the one that passes through the gas chromatographic column. Then, once performed calculation of constant K, this one is utilized for determining the carrier feeding pressure necessary to have a desired value of flow rate in the course of analysis, and now whatever kind of injector be utilized, the above mentioned condition of pneumatic closing system towards the exterior is no more to occur.

Thus, in case the gas chromatofraph utilizes an injector of split-splitless type, the calculation of constant K is performed closing the splitting line and the purge line of septum, so that all the carrier introduced streams through the column. When, then, the gas chromatograph is utilized, since the flow rate is controlled as a function of pressure, the opening of the splitting line and of the purge line determines an increase in the fed carrier flow rate, in equal conditions of pressure, whereas (in equal other contitions) the flow fed at the column downstream of splitting line remains unvaried. If the injector utilized is of on column type, then it will be necessary all the flow rate of the carrier gas fed for calculating costant should stream through the injector and the column, while an occasional dispersion of carrier from the injector introduction, during injection, does not influence correct determination of flow fed at column on the basis of pressure control.

Remarkably, it is possible to set in control panel 16 a desired pressure value instead of a desired flow value. In this case, formula (V) again transcribed as follows:

$$F_{stc} = K \frac{pi^2 - po^2}{T^{1,7}}$$

gives the calculated flow rate, translated into standard conditions

Figure 2:
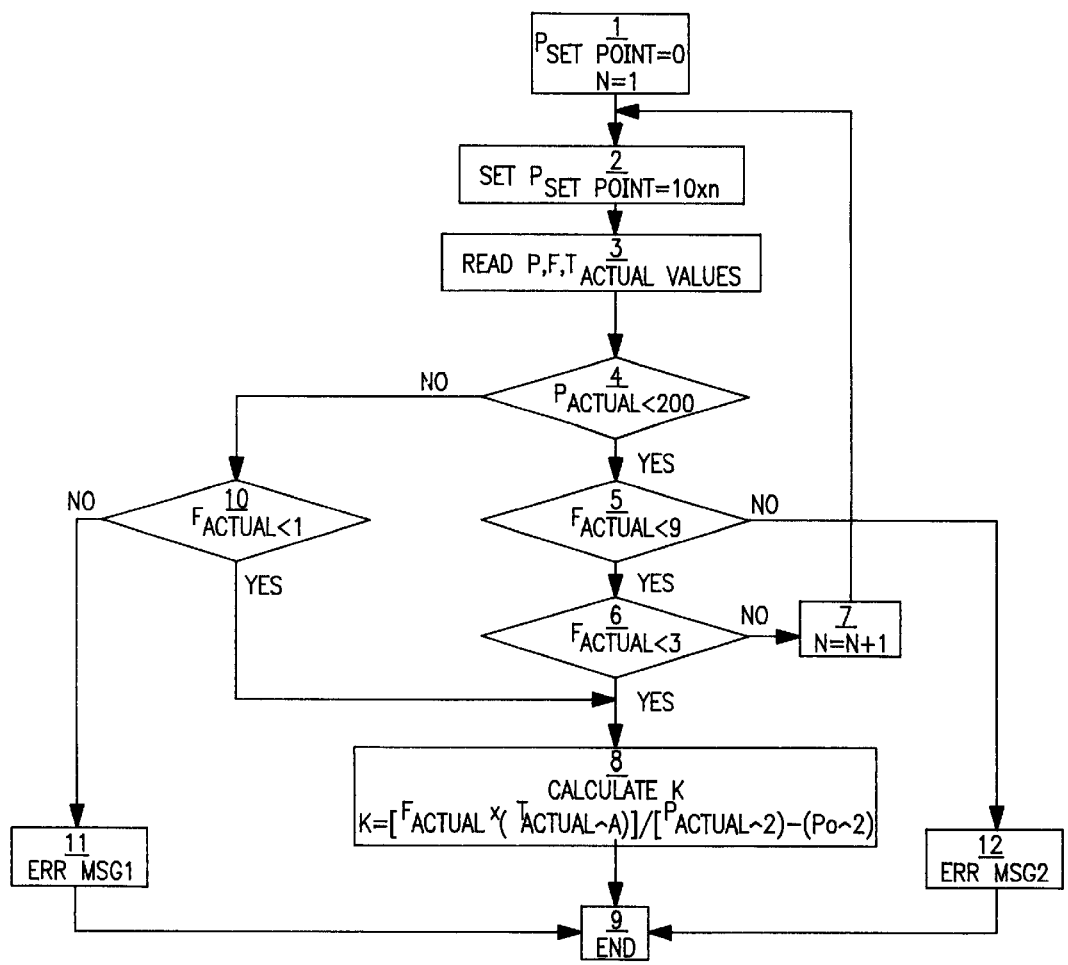
FIG. 2 shows a flow diagram utilized for calculating constant K.

In FIG. 2 is depicted a flowchart that can be utilized for calculating constant K through the automatic setting of pressure.

The system starts setting a pressure of 10 kPa and increasing it by 10 kPa steps till flow detector 13 detects a flow rate sufficiently high to be measured with accuracy. In particular, setting n=1, at step 1 it is set at step 2 the first pressure value desired (10 kPa) and at step 3 there are detected the actual pressure, temperature and flow rate values.

Actual pressure is controlled at step 4 so as to verify its being inferior to a preset limit (for instance 20 kPa), and this being verified, at step 5 the flow rate is controlled to verify its being within the upper limit of detector 13 operative range (for instance its being lesser than 9 sccm), while at step 6 it is verified the flow rate being superior to the limit of good reading of detector (for instance, being greater than 3 sccm).

If this latter condition has not been verified, the loop is repeated by increasing value n (step 7) by 1 and then the value of the set pressure by 10 kPa.

When all conditions at step 4, 5 and 6 have been verified, there is consent to calculate constant K (step 8) and to bring procedure (step 9) to an end.

If condition at step 5 has not been verified (excessive flow rate) the apparatus signals error (step 12), indicating that the circuit fluid resistance is too low.

If condition at step 4 has not been verified (excessive pressure), the system controls the flow rate value to verify if anyhow it falls within detector 13 operative range (for instance, flow rate greater than 1 sccm).

In this case constant K is calculated (step 8) and procedure brought to an end (step 9) Otherwise, an error message is sent (step 11) indicating the circuit fluid resistance is too high.

The above described method for controlling carrier gas flow rate can as well be utilized, as alternative or complementary to the function indicated, to effect a pneumatic control system, verifying no dispersion exists, such as may occur particularly in the connecting areas of column with injector.

In order to verify this it is sufficient, applying a first operating mode, to determine parameters and calculate constant K in two different conditions of oven temperature. If values different from constant K are obtained, it means there are leaks in the system. In a second operating mode, once parameters are determined and constant K calculated, should there occur variances between the carrier flow calculated and the one detected—obviously in equilibrium conditions of the system—this would indicate the existence of leaks in the system, which occurred after calculating constant K.

EXAMPLE

Initially it was arranged to calculate constant K utilizing a FISONS GC 8000 gas chromatograph with split-splitless injector and FID detector, in which there operates a capillary gas chromatographic column J & W in melted silica, having 0.32 mm inner diameter, 18 m length, stationary phase SEb2 0.4 mm thick.

The carrier gas utilized was helium (He).

In order to calculate K the injector was set so that the splitting flux and the washing flux of the septum were null, while the chamber was placed at a 50° C. (323° K) temperature. By setting different values of carrier feeding pressure the following corresponding results were obtained:

| set pressure (relative kPa) | measured pressure (relative kPa) | measured mass flow (ml/min standard) |
|---|---|---|
| 10 | 10 | 0.35 |
| 20 | 20 | 0.69 |
| 30 | 30 | 1.08 |
| 40 | 40 | 1.50 |
| 50 | 50 | 1.99 |
| 60 | 60 | 2.44 |
| 70 | 70 | 2.96 |
| 80 | 80 | 3.51 |

Since the condition to achieve the best measure range was $Fm \leq 3$ ml/min, the last condition was assumed for calculating constant K:

$K = (Fm \times T^{1.7})/(p_i^2 - p_o^2)$.

subtracting the numeric values:
$p_i = 80$ kPa relative $= 181$ kPa absolute
$p_o = 101$ kPa absolute
$T = 50°$ C. $= 323°$ K
$F = 3.51$ ml/min standard
$K = (3.51 \times 323^{1.7})/(181^2 - 101^2)$
$K = 2.868$ ml/min $K^{1.7}$ kPa$^2$ This value was stored and next a simulated analysis was performed maintaining the mass flow constant by controlling the carrier feeding pressure.

The oven temperature was set so as to vary between 50° C. and 200° C. with 20° C./min speed and the mass flow rate at column was set at constant value of 2.5 ml/min standard, with a splitting flux equal to 50 ml/min and a washing flux of septum equal to 2.5 ml/min (total flux: 55 ml/min).

Feeding pressure was set on the basis of value calculated each time:

$p_i = 101^2 + (2.5 \times T^{1.7})/2.868$ wherein T varies from 50° to 200° C. (from 323° to 473° K)

The flow at column was controlled by means of a flow meter set downstream of column, at the place of detector.

Figure 3:
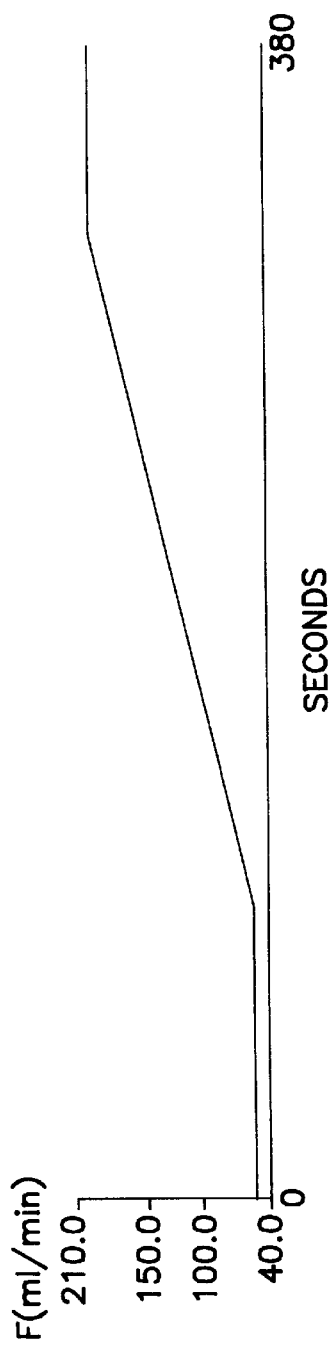
FIGS. 3, 4 and 5 are three graphs, representing respectively the variations in time of oven temperature, of carrier feeding pressure and carrier flow in column, during a simulated analysis, effected controlling the carrier pressure according to the invention to keep the flow constant with respect to the variation of oven temperature.
Figure 4:
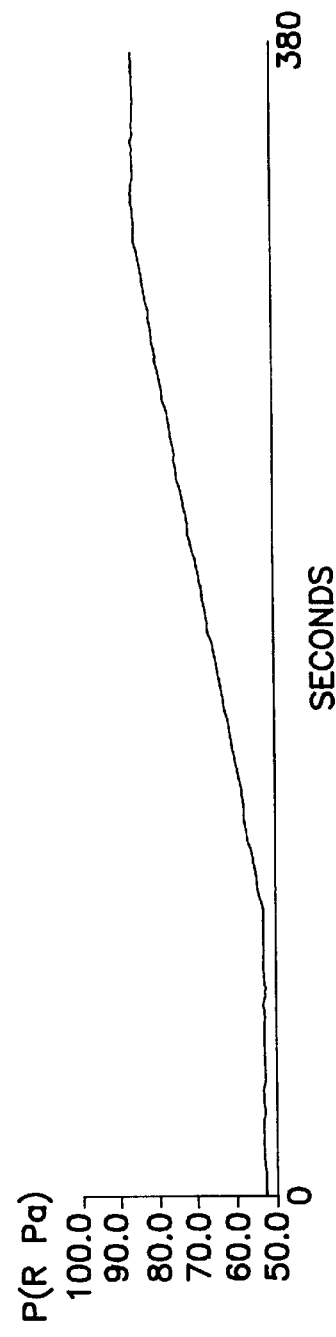
Figure 5:
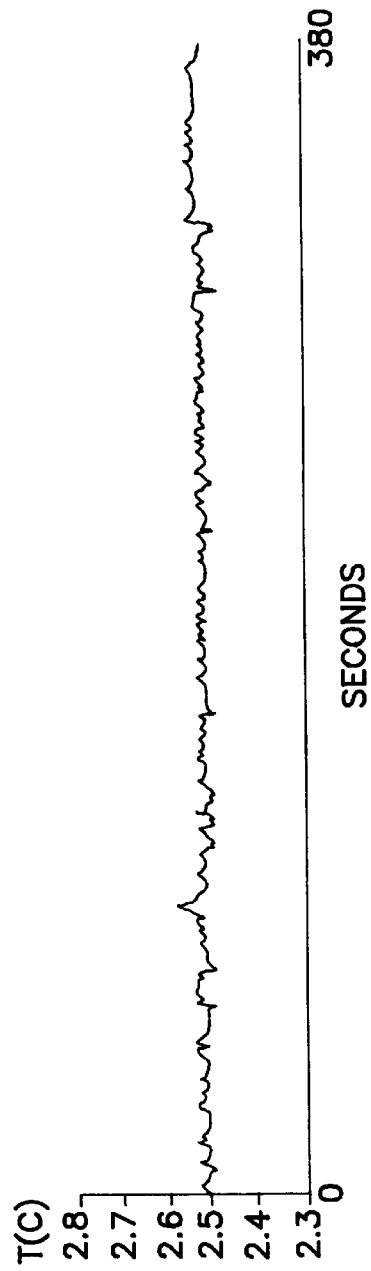

There were obtained, in the function of time, three graphs depicted in FIGS. 3, 4 and 5, which show respectively the temperature variations programmed, the carier feeding pressure variations calculated and the consequent flow variations, as detected downstream of the column.

We claim:

1. A method for controlling carrier gas flow rate through a gas chromatographic apparatus with capillary column subjected to temperature variations, by controlling the carrier gas feed pressure following computerized processing of equation (1) of carrier gas flow variation as a function of carrier gas pressure, of chromatographic column temperature, of system structural parameters and of gas parameters, said equation (1) is $$F_o T = \frac{\pi d^4}{256 L} \frac{1}{\eta} \frac{p_i^2 - p_o^2}{p_o}, \quad (1)$$

wherein $F_o^T$ is carrier flow rate at, $p_i$ is inlet carrier gas pressure, $p_o$ is carrier gas outlet pressure, L is the length of the capillary column, $\eta$ is viscosity of the carrier gas, and d is inner diameter of the capillary tube, said method comprising:

preliminarily passing a carrier gas through the apparatus, detecting pressure values, temperature and flow under stabilized conditions;

preliminarily calculating a constant $K_1$ representing the system structural parameters based on the values detected and on said equation (1), said constant $K_1$ is $$K_1 = \frac{\pi d^4}{256 L};$$

applying said constant $K_1$ in said equation (1) for controlling carrier gas flow rate through calculation; and adjusting said carrier gas feed pressure thereby affecting the carrier gas flow rate while said gas chromatographic apparatus is being utilized.

2. The method according to claim 1, wherein a value of the term $1/\eta$ of said equation (1) is preliminarily entered.

3. A method for controlling carrier gas flow rate through a gas chromatographic apparatus with capillary column subjected to temperature variations, by controlling carrier gas feed pressure following computerized processing of equation (1') of carrier gas standard flow variation as a function of carrier gas pressure, of chromatographic column temperature, and of gas parameters, said equation (1') being $$F_{st} = \frac{\pi d^4}{256 L} \frac{1}{\eta} \frac{p_i^2 - p_o^2}{p_{st}} \frac{T_{st}}{T}, \quad (1')$$

wherein $F_{st}$ is carrier gas flow rate in standard conditions, $T_{st}$ is 298 degree K, $p_{st}$ is 1 atm., $P_i$ is the inlet carrier gas pressure, $p_o$ is the outlet carrier gas pressure, d is the inner diameter of the capillary column, L is the length of the capillary column, $\eta$ is the carrier gas viscosity, and T is the absolute temperature of an oven housing the capillary column, said method comprising:

preliminarily passing a carrier gas through the apparatus, detecting pressure values, temperature and flow under stabilized conditions;

preliminarily calculating a constant $K_1$ representing the structural parameters based on values detected and on application of said equation (1'), said constant $K_1$ is $$K_1 = \frac{\pi d^4}{256 L};$$

applying said constant $K_1$ in said equation (1') for controlling carrier gas flow rate through calculation; and adjusting said carrier gas feed pressure while said gas chromatographic apparatus is being utilized.

4. The method according to claim 3, wherein the carrier gas viscosity $\eta$ is obtained by empirical formula $$\eta = \eta_{st} \left( \frac{T}{T_{st}} \right)^{0.7},$$

wherein $\eta_{st}$ is the viscosity of the carrier gas in standard conditions, and T is the absolute temperature of said oven; wherein said formula (1') becomes $$F_{st} = \frac{\pi d^4}{256 L} \frac{1}{\eta_{st}} \frac{p_i^2 - p_o^2}{p_{st}} \left( \frac{T_{st}}{T} \right)^{1.7}; \quad (1'')$$

wherein a constant term $$K = \frac{\pi d^4}{256 L} \frac{1}{\eta_{st}} \frac{T_{st}^{1.7}}{p_{st}}$$

is calculated based on values detected and on application of aforesaid equation (1''); and wherein said constant K is applied in said equation (1″) for controlling carrier gas flow rate through calculation, and adjusting said carrier gas feed pressure while said gas chromatographic apparatus is being utilized.

5. A device for controlling carrier gas flow rate in a gas chromatographic apparatus, said device comprising: an oven housing a gas chromatographic capillary column, a sample injector upstream of the column and a detector downstream of the column, a feeding line of carrier gas to the injector, said device comprises means for detecting the feeding pressure of the carrier gas, means for detecting capillary column temperature in the oven, means for introducing data relative to carrier gas to desired flow rate, at least one control valve for the carrier gas and means for storing and processing data so as to control said valve on the basis of data stored and detected, in order to obtain feeding pressure of the carrier gas so as to produce—moment by moment and with reference to a carrier gas flow rate variation equation as a function of inlet pressure, of column temperature and of system structural parameters, said equation is $$F_o^T = \frac{\pi d^4}{256 \eta L} \cdot \frac{p_i^2 - p_o^2}{p_o},$$

wherein $F_o^T$ is the volumetric flow rate, $p_i$ is inlet pressure, $p_o$ is outlet pressure, L is the length of the capillary column, $\eta$ is viscosity of the gas, and d is inner diameter of the capillary tube the desire flow rate of the same carrier gas through the gas chromatographic capillary column, characterized in that there are provided means for detecting the carrier gas flow rate in a stabilized condition of its passage through the gas chromatographic apparatus and means for sending the data detected of carrier gas flow rate and pressure, and of column temperature to the processing means, so as to calculate and store a constant factor $K_1$ representing the structural data of the capillary column through which the carrier gas passes, wherein $$K_1 = \frac{\pi d^4}{256 L}.$$

6. A method for controlling carrier gas flow range through a gas chromatographic apparatus with capillary column subjected to temperature variations, with the purpose of verifying the existence of pneumatic leakages in system, characterized by computerized processing of equation of carrier gas flow variation as a function of inlet pressure, of column temperature and system structural parameters through: preliminary determination at least of system structural parameters by detecting pressure, temperature and flow rate values in stabilized conditions of carrier passage through apparatus and by calculating a constant representing said parameters on the basis of values detected and in application of mentioned equation; storing the mentioned constant; repeating the preliminary determination of system parameters in a stabilized condition other than the previous one at least for the column temperature; recalculating the mentioned constant and confronting results of the two calculations.

7. A method for controlling the carrier gas flow rate through a gas chromatographic apparatus with capillary column subjected to temperature variations, with the purpose of verifying the existence of pneumatic leakages in system, characterized in that it comprises the calculation of carrier gas pressure for obtaining a prefixed flow rate value, and comparison between such prefixed carrier value and the value read by a flowmeter operating in the system.

* * * * *